United States Patent
Cummins et al.

(10) Patent No.: US 11,291,573 B2
(45) Date of Patent: Apr. 5, 2022

(54) DELIVERY SYSTEM FOR A SELF-EXPANDING MEDICAL DEVICE

(71) Applicant: Cook Medical Technologies LLC, Bloomington, IN (US)

(72) Inventors: Sean Cummins, Limerick (IE); Dean R. Puckett, Bloomington, IN (US); Brent A. Mayle, Spencer, IN (US); James C. Merk, Terre Haute, IN (US); Tawnya Wood, Spencer, IN (US); Tiffani L. Cannon, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 875 days.

(21) Appl. No.: 14/209,097

(22) Filed: Mar. 13, 2014

(65) Prior Publication Data

US 2014/0277366 A1    Sep. 18, 2014

Related U.S. Application Data

(60) Provisional application No. 61/789,885, filed on Mar. 15, 2013.

(51) Int. Cl.
*A61F 2/966* (2013.01)
*A61F 2/95* (2013.01)

(52) U.S. Cl.
CPC ............. *A61F 2/966* (2013.01); *A61F 2/95* (2013.01); *A61F 2/9517* (2020.05); *A61F 2/9522* (2020.05); *A61F 2002/9505* (2013.01)

(58) Field of Classification Search
CPC .. A61F 2/966; A61F 2/95; A61F 2/962; A61F 2002/9517; A61F 2002/9505; A61F 2002/9522
See application file for complete search history.

(56) References Cited

U.S. PATENT DOCUMENTS

| 4,581,025 A | 4/1986 | Timmermans |
| 4,665,918 A | 5/1987 | Garza et al. |
| 4,875,480 A | 10/1989 | Imbert |

(Continued)

FOREIGN PATENT DOCUMENTS

| WO | WO 87/04935 | 8/1987 |
| WO | WO 2006/014233 A2 | 2/2006 |

OTHER PUBLICATIONS

Kiemeneij et al., "Cost comparison between two modes of Palmaz Scatz coronary stent implementation: transradial bare stent technique vs. transfemoral sheath-protected stent technique", Cathet Cariovasc Diagn. Aug. 1995; 35(4): 301-8, discussion 309. (http://www.ncbi.nlm.nih.gov/pubmed/7497502).

*Primary Examiner* — Elizabeth Houston
*Assistant Examiner* — Michael G Mendoza
(74) *Attorney, Agent, or Firm* — Crowell & Moring LLP

(57) ABSTRACT

A delivery system is provided for self-expanding medical devices, such as stents. The delivery system has a restraining sheath that maintains the stent in a compressed state prior to deployment. The restraining sheath terminates distally from the deployment handle, and a wire connects the restraining sheath to the deployment handle. The restraining sheath is withdrawn from the stent to deploy the stent by pulling the wires proximally at the deployment handle.

10 Claims, 8 Drawing Sheets

(56) References Cited

U.S. PATENT DOCUMENTS

| | | |
|---|---|---|
| 4,950,227 A | 8/1990 | Savin et al. |
| 5,026,377 A | 6/1991 | Burton et al. |
| 5,360,401 A | 11/1994 | Turnland et al. |
| 5,405,378 A | 4/1995 | Strecker |
| 5,456,694 A | 10/1995 | Marin et al. |
| 5,474,563 A | 12/1995 | Myler et al. |
| 5,534,007 A | 7/1996 | St. Germain et al. |
| 5,571,168 A | 11/1996 | Toro |
| 5,643,278 A | 7/1997 | Wijay |
| 5,647,857 A | 7/1997 | Anderson et al. |
| 5,662,703 A | 9/1997 | Yurek et al. |
| 5,690,644 A | 11/1997 | Yurek et al. |
| 5,743,874 A | 4/1998 | Fischell et al. |
| 5,771,168 A | 6/1998 | Liao et al. |
| 5,772,669 A | 6/1998 | Vrba |
| 5,776,141 A | 7/1998 | Klein et al. |
| 5,788,707 A | 8/1998 | Del Toro et al. |
| 5,797,952 A | 8/1998 | Klein |
| 5,993,460 A | 11/1999 | Beitelia et al. |
| 6,042,588 A | 3/2000 | Munsinger et al. |
| 6,238,402 B1 | 5/2001 | Sullivan, III et al. |
| 6,273,895 B1 | 8/2001 | Pinchuk et al. |
| 6,302,906 B1 | 10/2001 | Goicoechea et al. |
| 6,572,645 B2 | 6/2003 | Leonhardt |
| 6,607,551 B1 | 8/2003 | Sullivan et al. |
| 6,660,031 B2 | 12/2003 | Tran et al. |
| 6,676,666 B2 | 1/2004 | Vrba et al. |
| 6,736,839 B2 | 5/2004 | Cummings |
| 6,773,446 B1 | 8/2004 | Dwyer et al. |
| 7,052,511 B2 | 5/2006 | Weldon et al. |
| 7,285,130 B2 | 10/2007 | Austin |
| 7,300,456 B2 | 11/2007 | Andreas et al. |
| 7,387,640 B2 | 6/2008 | Cummings |
| 7,635,382 B2 | 12/2009 | Pryor |
| 7,651,521 B2 | 1/2010 | Ton et al. |
| 7,815,669 B2 | 10/2010 | Matsuoka et al. |
| 7,935,141 B2 | 5/2011 | Randall et al. |
| 7,967,829 B2 | 6/2011 | Gunderson et al. |
| 8,025,692 B2 | 9/2011 | Feeser |
| 8,075,606 B2 | 12/2011 | Dorn |
| 8,182,522 B2 | 5/2012 | Sarac et al. |
| 8,262,718 B2 | 9/2012 | Chuter et al. |
| 8,323,326 B2 | 12/2012 | Dorn et al. |
| 8,366,760 B2 | 2/2013 | Kumoyama |
| 8,366,761 B2 | 2/2013 | Paul et al. |
| 8,419,784 B2 | 4/2013 | Matsuoka et al. |
| 8,435,279 B2 | 5/2013 | Beyerlein et al. |
| 2001/0027323 A1 | 10/2001 | Sullivan, III et al. |
| 2001/0032850 A1 | 10/2001 | Neuner |
| 2001/0034548 A1 | 10/2001 | Vrba et al. |
| 2002/0029075 A1 | 3/2002 | Leonhardt |
| 2002/0103525 A1 | 8/2002 | Cummings |
| 2005/0004553 A1 | 1/2005 | Douk |
| 2005/0033403 A1 | 2/2005 | Ward et al. |
| 2005/0080476 A1 | 4/2005 | Gunderson et al. |
| 2005/0209671 A1 | 9/2005 | Ton et al. |
| 2005/0240254 A1 | 10/2005 | Austin |
| 2006/0036314 A1 | 2/2006 | Perez et al. |
| 2006/0259124 A1 | 11/2006 | Matsuoka et al. |
| 2006/0282152 A1* | 12/2006 | Beyerlein .............. A61F 2/95 623/1.11 |
| 2007/0032850 A1 | 2/2007 | Ruiz et al. |
| 2007/0055340 A1* | 3/2007 | Pryor .................. A61F 2/95 623/1.11 |
| 2007/0060999 A1 | 3/2007 | Randall et al. |
| 2007/0168014 A1 | 7/2007 | Jimenez et al. |
| 2007/0191925 A1 | 8/2007 | Dorn |
| 2007/0219617 A1 | 9/2007 | Saint |
| 2007/0260301 A1 | 11/2007 | Chuter et al. |
| 2009/0125093 A1* | 5/2009 | Hansen ................ A61F 2/95 623/1.11 |
| 2009/0312831 A1 | 12/2009 | Dorn |
| 2010/0049297 A1 | 2/2010 | Dorn |
| 2010/0076541 A1 | 3/2010 | Kumoyama |
| 2010/0145309 A1 | 6/2010 | Tollner et al. |
| 2010/0168834 A1 | 7/2010 | Ryan et al. |
| 2011/0009943 A1 | 1/2011 | Paul et al. |
| 2011/0172686 A1 | 7/2011 | Gifford, III et al. |
| 2011/0213450 A1 | 9/2011 | Maclean et al. |
| 2011/0295354 A1 | 12/2011 | Bueche et al. |
| 2011/0301689 A1* | 12/2011 | Dorn .................... A61F 2/95 623/1.12 |
| 2012/0016454 A1 | 1/2012 | Jantzen et al. |
| 2012/0022635 A1 | 1/2012 | Yamashita |
| 2012/0083869 A1 | 4/2012 | Wubbeling et al. |
| 2012/0123517 A1 | 5/2012 | Ouellette et al. |
| 2012/0143304 A1 | 6/2012 | Wubbeling et al. |
| 2012/0172968 A1 | 7/2012 | Chuter et al. |

* cited by examiner

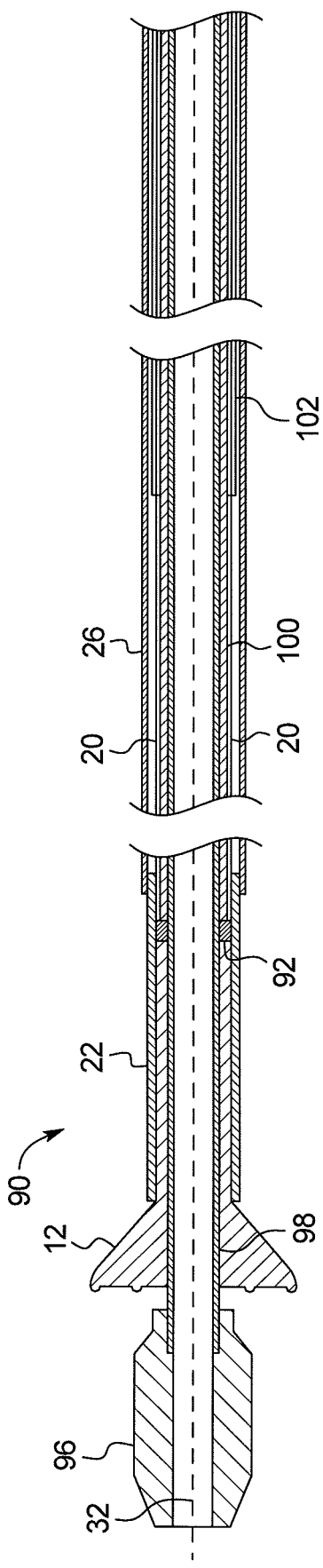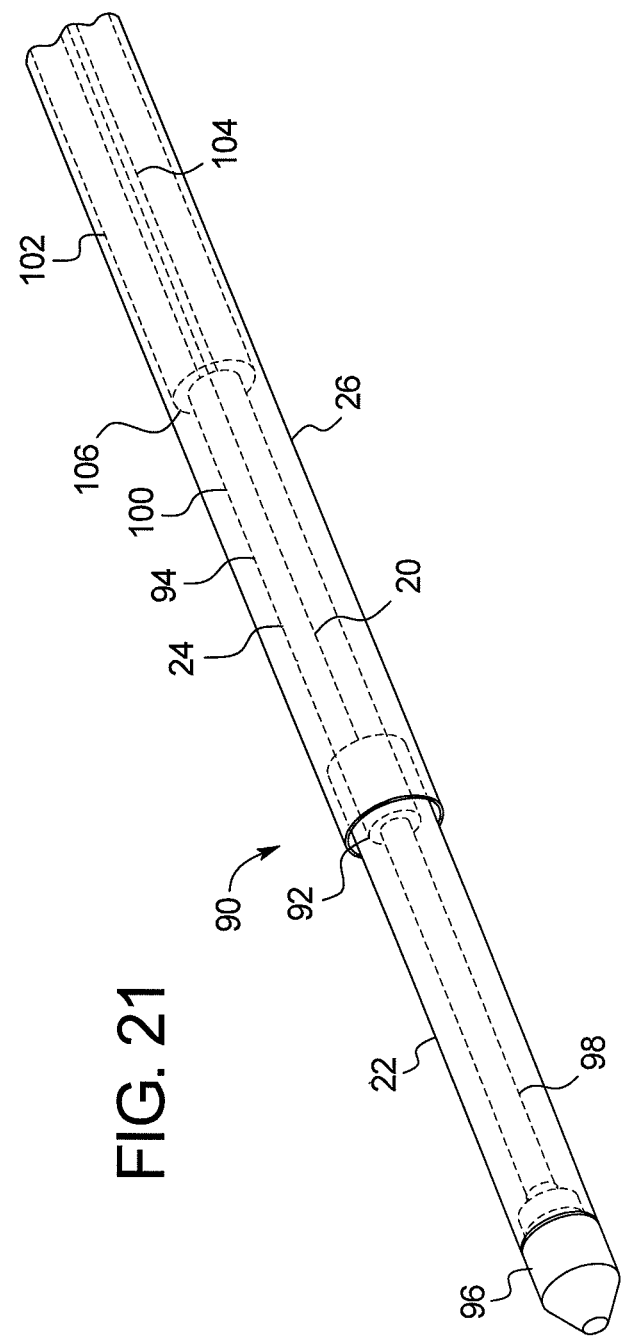

DELIVERY SYSTEM FOR A SELF-EXPANDING MEDICAL DEVICE

This application claims priority to U.S. Provisional Application No. 61/789,885, filed Mar. 15, 2013, which is hereby incorporated by reference herein.

BACKGROUND

The present invention relates generally to medical devices and more particularly to delivery systems for medical devices.

Intraluminal medical devices are used by physicians to treat numerous conditions using minimally invasive procedures. Examples of intraluminal medical devices include stents, stent-grafts, filters, valves, etc. One type of intraluminal medical device that has become especially common is self-expanding stents. Typically, self-expanding medical devices, including stents, are made from an elastic structure that may be compressed into a low profile state that can be passed through vessels in a patient with minimal trauma. Once at the desired treatment site, the self-expanding medical device is released and self-expands like a spring until it contacts a tissue wall which prevents further expansion. Common materials that are used in self-expanding medical devices include nitinol and stainless steel, although other materials are also possible.

Self-expanding stents are used to treat various organs, such as the vascular system, colon, biliary tract, urinary tract, esophagus, trachea and the like. For example, stents are commonly used to treat blockages, occlusions, narrowing ailments and other similar problems that restrict flow through a passageway. One area where stents are commonly used for treatment involves implanting an endovascular stent into the vascular system in order to improve or maintain blood flow through narrowed arteries. However, stents are also used in other treatments as well, such as the treatment of aneurysms. Stents have been shown to be useful in treating various vessels throughout the vascular system, including both coronary vessels and peripheral vessels (e.g., carotid, brachial, renal, iliac and femoral). In addition, stents have been used in other body vessels as well, such as the digestive tract.

One type of delivery system for intraluminal medical devices includes an inner catheter and an outer sheath attached to a handle arrangement. One portion of the handle is typically connected to the inner catheter and another portion of the handle is typically connected to the outer sheath. The inner catheter extends coaxially through the outer sheath, and the two portions of the handle are arranged to longitudinally pull the outer sheath relative to the inner catheter. Thus, when the distal end of the delivery system is positioned within the patient's body at the intended treatment site, the physician actuates the handle outside the patient's body by moving the two portions relative to each other so that the outer sheath is withdrawn over the medical device and inner catheter. In the case of self-expanding medical devices, like stents, the outer sheath also serves to radially restrain the device in the compressed state until the outer sheath is withdrawn. As the outer sheath is withdrawn, the medical device is released in the body at the treatment site, and in the case of a self-expanding stent, the stent expands outward away from the inner catheter and presses against the vessel wall. Although the outer sheath is usually withdrawn by pulling the outer sheath proximally relative to the inner catheter, it may also be possible to withdraw the outer sheath by pushing the inner catheter distally relative to the outer sheath. After the medical device has been fully released from the delivery system, the handle may then be pulled by the physician to withdraw the inner catheter and outer sheath from the patient's body, while leaving the medical device implanted in the body.

Precise placement of intraluminal medical devices is a concern in most medical procedures. One problem that can contribute to imprecise placement of intraluminal medical devices is deflection of the delivery system during deployment. This can be a particular problem in the deployment of self-expanding medical devices, like stents, because the medical device presses outward against the inner surface of the outer sheath prior to deployment. When the outer sheath is withdrawn, the outward pressure exerted by the medical device creates friction between the medical device and the outer sheath. Since the medical device is typically prevented from moving proximally with the outer sheath by a stop attached to the inner catheter, the frictional force between the medical device and the outer sheath causes the outer sheath to be in tension and the inner catheter to be in compression. This can cause the outer sheath to stretch in length due to the tensile force. In addition, the force required to withdraw the outer sheath can be especially high. As a result, it can be difficult for a physician to accurately control deployment of the medical device.

Accordingly, the inventors believe it would be desirable to provide an improved delivery system for intraluminal medical devices.

SUMMARY

A delivery system is described for self-expanding medical devices. The delivery system has an inner catheter with a stop surface that extends from the proximal end of the medical device to a deployment handle. A restraining sheath surrounds the medical device and prevents the medical device from expanding prior to deployment. The proximal end of the restraining sheath terminates distally from the deployment handle. A wire is adhered to the restraining sheath and extends from the restraining sheath to the deployment handle. The medical device is deployed by pulling on the wire which causes the restraining sheath to withdraw proximally from the medical device. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 20 is a cross-sectional view of another delivery system;

FIG. 21 is a perspective view of the delivery system;

DETAILED DESCRIPTION

Figure 1:
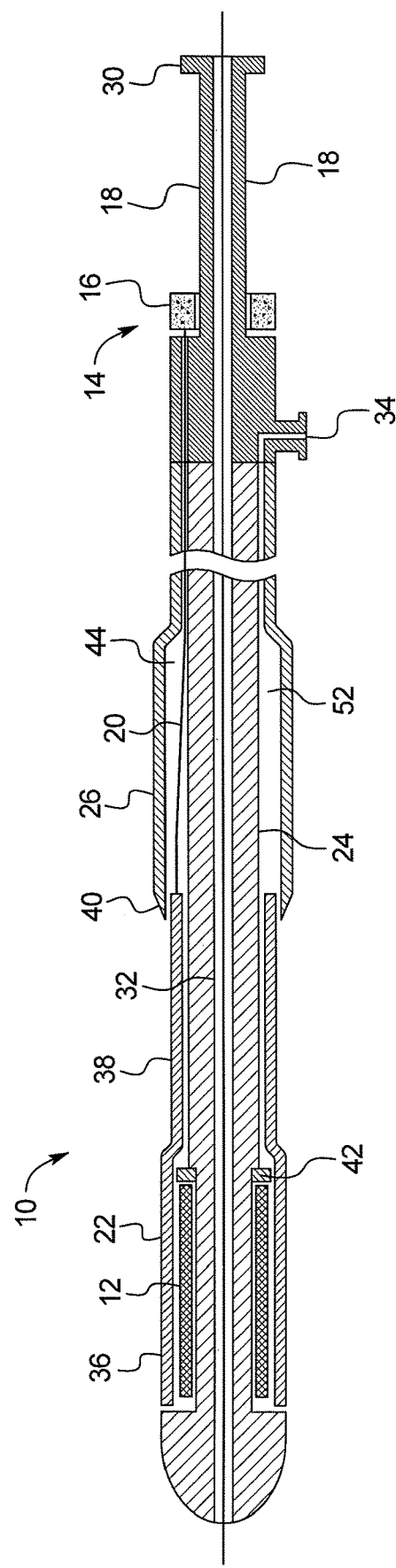
FIG. 1 is a cross-sectional view of a delivery system.

Referring now to the figures, and particularly to FIG. 1, a delivery system 10 for a self-expanding medical device 12 is shown. As shown in FIG. 1, the delivery system 10 includes a deployment handle 14 with first and second handle members 16, 18. The first handle member 16 is attached to a wire 20 connected to a restraining sheath 22, and the second handle member 18 is attached to an inner catheter 24. Preferably, a covering sheath 26 is also attached to the second handle member 18. The deployment handle 14 may also have a guide section 28 to control proximal movement of the first handle member 16 and a proximal stop 30 to limit proximal travel of the first handle member 16. However, it should be understood that the delivery system 10 may be used with numerous types of deployment handles including deployment handles that wind up the wire 20 during deployment. Although it may be possible to design the delivery system 10 as a rapid-exchange system, the delivery system 10 is preferably an over-the-wire system where the guide wire lumen 37 extends from the distal end of the inner catheter 24 to the deployment handle 14. The deployment handle 14 is also preferably provided with a flushing port 34 that is in communication with the annular space between the covering sheath 26 and the inner catheter 24 and between the restraining sheath 22 and the inner catheter 24. Although various types of medical devices 12 may be used in the delivery system 10, a self-expanding stent 12 made from nitinol is one preferred type of medical device 12 that may be used.

As shown in FIG. 1, the restraining sheath 22 may have a first portion 36 that extends along the length of the stent 12 and a second portion 38 that extends proximally from the proximal end of the stent 12. The first portion 36 is sized to circumferentially restrain the stent 12 in a compressed state and prevent the stent 12 from expanding until the restraining sheath 22 is withdrawn from the stent 12 by pulling the wires 20. Preferably, the second portion 38 is no longer than about 2 times the length of the stent 12. As shown in FIG. 1, the second portion 38 of the restraining sheath 22 may have a smaller outer profile compared to the first portion 36. Where the second portion 38 is smaller than the first portion 36, the second portion 38 is preferably at least as long as the stent 12 so that the second portion 38 has enough length to slide through the covering sheath 26 without the first portion 36 sliding into the covering sheath 26 during deployment. Alternatively, the entire length of the restraining sheath 22 may have a generally constant profile. The restraining sheath 22 may also terminate near the proximal end of the stent 12 if desired.

The covering sheath 26 is preferably fixed to the deployment handle 14 and does not move during deployment of the stent 12. The covering sheath 26 may be desirable to contain the wires 20 and provide an annular lumen to direct flushing fluid from the flushing port 34 through the delivery system 10. The covering sheath 26 may also provide additional robustness to the delivery system 10. Preferably, the distal end of the covering sheath 26 extends over at least the proximal end of the restraining sheath 22. However, it is preferred that the covering sheath 26 not extend over the portion of the restraining sheath 22 that encompasses the stent 12. That is, the distal end of the covering sheath 26 preferably extends over only the portion of the restraining sheath 22 that extends proximally from the proximal end of the stent 12. The distal end of the covering sheath 26 may be provided with an atraumatic tapered end 40 that provides a smooth transition between the restraining sheath 22 and the covering sheath 26. The distal end of the covering sheath 26 may also be provided with an inner diameter that fits closely onto the outer diameter of the restraining sheath 22 to present a smooth transition and to minimize leakage of flushing fluid between the restraining sheath 22 and the covering sheath 26.

The inner catheter 24 has a stop surface 42 that abuts the proximal end of the stent 12 during deployment to prevent the stent 12 from moving proximally during deployment. The stop surface 42 may be a metal or polymer ring bonded to the inner catheter 24 or may be an integral step on the inner catheter 24. As shown in FIG. 1, the proximal end of the restraining sheath 22 terminates distally from the deployment handle 14 so that the deployment handle 14 and the restraining sheath 22 are separated by a longitudinal space 44. The longitudinal space 44 must be at least as long as the longest stent 12 used in the delivery system 10 to allow enough travel to withdraw the restraining sheath 22 from the stent 12. One or more wires 20 are attached to the restraining sheath 22 that extend across the space 44 between the restraining sheath 22 and the deployment handle 14. Preferably, multiple wires 20 are used that are equally spaced circumferentially around the inner catheter 24. The proximal end of the wires 20 may be attached to the first handle member 16 or any type of mechanism designed to pull the wires 20. Thus, the stent 12 may be deployed by pulling on the wires 20 to proximally withdraw the restraining sheath 22 away from the stent 12. Since the stop surface 42 prevents the stent 12 from moving proximally with the restraining sheath 22, the restraining sheath 22 uncovers the stent 12 as it moves proximally. As a result, the stent 12 is allowed to self-expand toward a vessel wall and radially away from the inner catheter 24.

Figure 3:
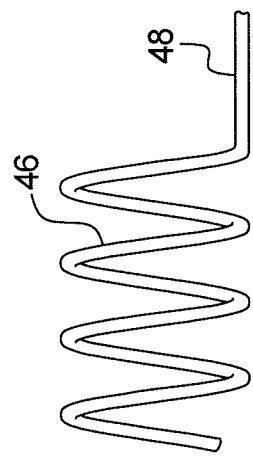
FIG. 3 is a side view of a wire.
Figure 2:
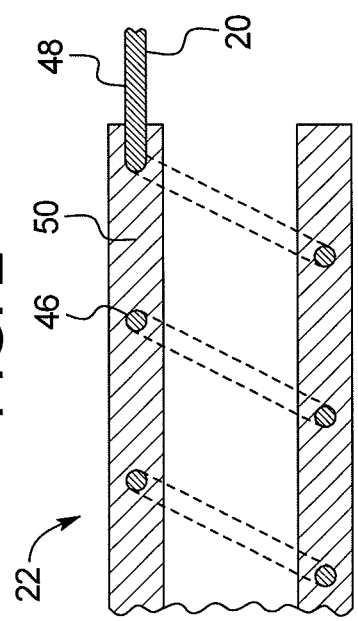
FIG. 2 is a cross-sectional view of a portion of a restraining sheath.

As shown in FIGS. 2-3, the wire 20 may have a coiled portion 46 and a straight portion 48. The coiled portion 46 is adhered to the restraining sheath 22 to fix the wire 20 and restraining sheath 22 together. For example, the restraining sheath 22 may be made out of a thermoplastic polymer 50 like nylon, and the coiled portion 46 may be embedded within the thermoplastic polymer 50 like in FIG. 2 so that the thermoplastic polymer 50 covers the coiled portion 46. The attachment of the coiled portion 46 to the restraining sheath 22 provides a stronger connection between the restraining sheath 22 and the wire 20 compared to if the restraining sheath 22 and a wire 20 were only attached along the straight portion 46 of the wire 20. At the transition between the coiled portion 46 and the straight portion 48, the wire 20 bends away from the helical path of the coiled portion 46 and extends generally parallel to the axis of the coiled portion 46. Preferably, the transition between the coiled portion 46 and the straight portion 48 is located distal from the proximal end of the restraining sheath 22, although a part of the coiled portion 46 could extend proximally from the proximal end of the restraining sheath 22. The straight portion 48 extends proximally from the restraining sheath 22, and as shown in FIG. 1, the straight portion 48 extends across the space 44 between the restraining sheath 22 and the deployment handle 14 and through the annular space 52 between the covering sheath 26 and the inner catheter 24. Although the wire 20 may have various cross-sectional shapes, such as rectangular, the cross-section of the wire is preferably round.

In FIG. 2, the coiled portion 46 of the wire 20 may have a single coiled diameter and may extend only along the second portion 38 of the restraining sheath 22 where the second portion 38 is smaller in diameter than the first portion 36 like FIG. 1. Alternatively, where the restraining sheath 22 has a single diameter along its length like in FIGS. 10 and 20, a single diameter coiled portion 46 like in FIGS. 2-3 may extend along a part of the first portion 36 of the restraining sheath 22. For example, the coiled portion 46 of the wire 20 could extend along at least half the length of the stent 12 or along the entire length of the stent 12.

Figure 5:
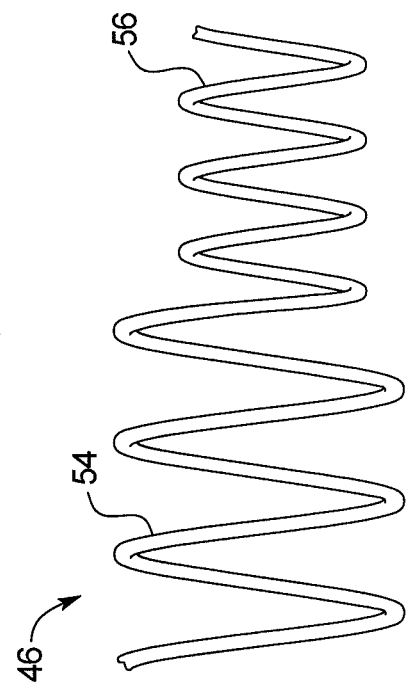
FIG. 5 is a side view of another wire.
Figure 4:
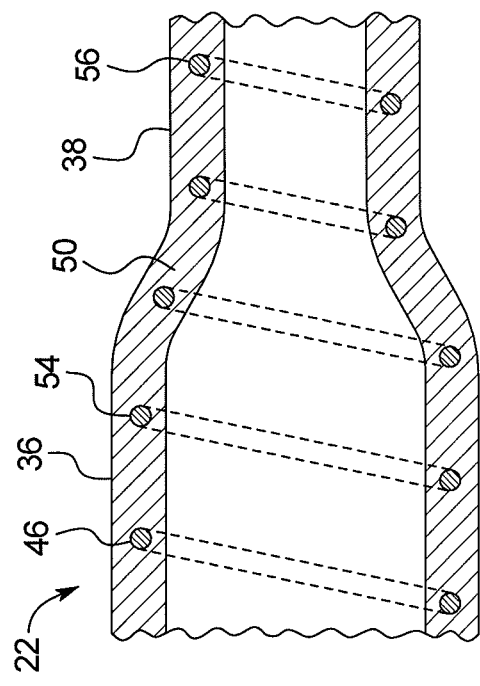
FIG. 4 is a cross-sectional view of a portion of another restraining sheath.

As shown in FIGS. 4-5, the coiled portion 46 of the wire 20 may have a first section 54 with a coiled diameter that is larger than the coiled diameter of the second section 56. This arrangement may be useful with the restraining sheath 22 of FIG. 1, where the first portion 36 has inner and outer circumferences that are larger than the inner and outer circumferences of the second portion 38. Thus, the first section 54 of the coiled portion 46 may extend along a portion of the length of the stent 12, and the second section 56 may extend proximally from the stent 12. As noted above, the first section 54 may extend along at least half the length of the stent 12 or along the entire length of the stent 12.

Figure 7:
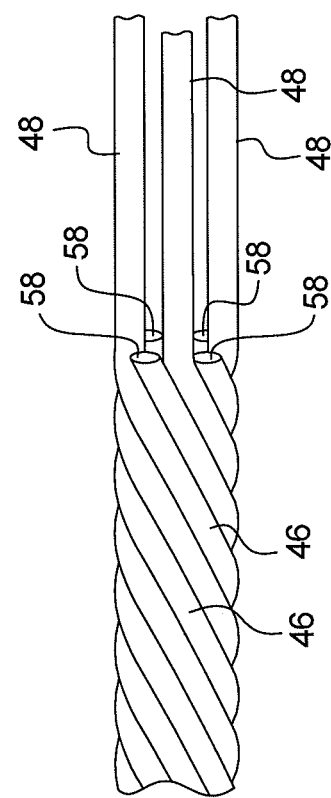
FIG. 7 is a side view of wires with interleaved coiled portions and coiled wires.
Figure 6:
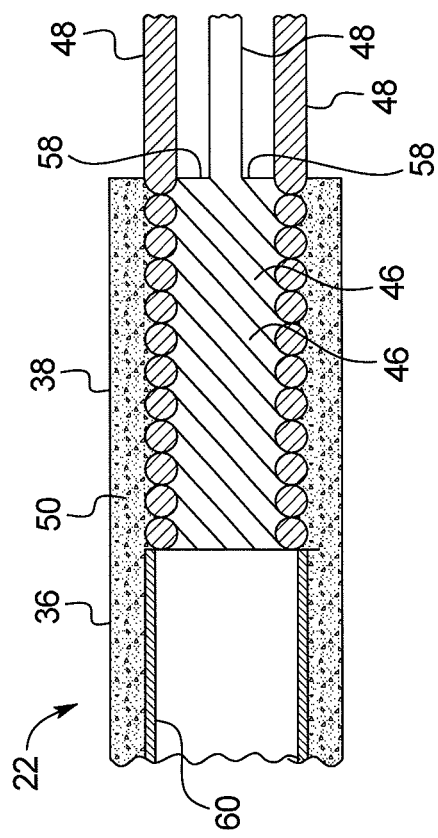
FIG. 6 is a cross-sectional view of a portion of another restraining sheath.
Figure 8:
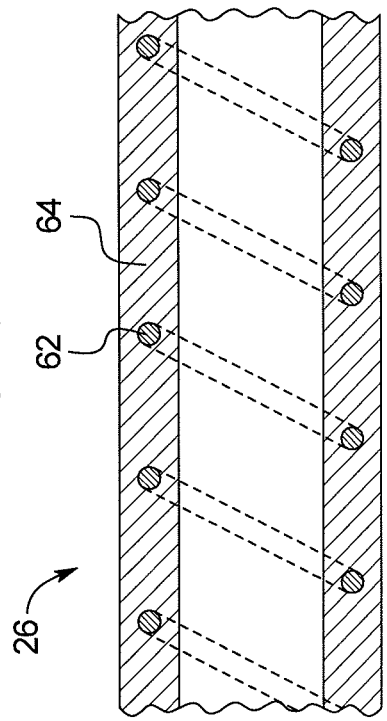
FIG. 8 is a cross-sectional view of a covering sheath.

As shown in FIG. 6, multiple wires 20 may be adhered to the restraining sheath 22. For example, it may be desirable to have at least two wires 20 equally spaced around the inner catheter 24. Where the wires 20 have coiled portions 46 adhered to the restraining sheath 22, the coiled portions 46 of the wires 20 may be spaced away from each other so that the coiled portions 46 fit within each other without interfering. The coiled portions 46 may also be oriented relative to each other so that the straight portions 48 are circumferentially spaced around the inner catheter 24. As also shown FIGS. 6-7, coiled wires 58 that do not extend proximally to the deployment handle 14 may also be spaced between the coiled portions 46. In contrast to the wires 20 that have a coiled portion 46 and a straight portion 48, the coiled wires 58 may only be coiled without having a straight portion. The coiled wires 58 may also terminate where the wires 20 transition between the coiled portion 46 and the straight portion 48 or distally from the transition. As shown in FIGS. 6-7, it may also be desirable for the coiled portions 46 and coiled wires 58 to abut against each other along the restraining sheath 22 to form a closed coil tube. As shown in FIG. 6, it may be possible in this embodiment for the thermoplastic polymer 50 to only cover the coiled portions 46 and the coiled wires 58 without being disposed along the inner surface of the coiled portions 46 and coiled wires 58. This may be desirable to reduce the profile of the restraining sheath 22. A low friction liner 60, such as polytetrafluoroethylene (PTFE), may also be disposed along the inner surface of at least the first portion 36 of the restraining sheath 22 that extends along the stent 12. This may be useful to reduce the friction between the restraining sheath 22 and the stent 12 to lower the force required to withdraw the restraining sheath 22. For example, as shown in FIG. 6, the coiled portions 46 of the wires 20 and the coiled wires 58 without a straight portion may extend only along the second portion 38 of the restraining sheath 22 proximally from the stent 12. The liner 60 may then extend along the length of the stent 12 and contact the outer surface of the stent 12. The thermoplastic polymer 50 may cover the coiled portions 46 of the wires 20, the coiled wires 58 and the liner 60 to adhere all of the components together. The embodiment of FIG. 6 may be used with a restraining sheath 22 like FIG. 1 with a larger first portion 36 and smaller second portion 38, or may also be used with a restraining sheath 22 like FIGS. 10 and 20 where the restraining sheath 22 has a constant circumference along its length.

As shown in FIG. 7, it may also be desirable to provide the covering sheath 26 with a coiled wire 62 embedded within a thermoplastic polymer 64. This may be useful to strengthen the covering sheath 26 to minimize buckling of the inner catheter 24 within the covering sheath 26.

Another embodiment of the delivery system 66 is shown in FIGS. 9-19. For conciseness, features of the delivery system 10 that have been described above are not repeated below, since one of ordinary skill in the art will understand that the principles described above could be used with different types of delivered delivery systems including the delivery systems 66, 90 of FIGS. 9-19 and 20-23. One advantage of the delivery systems 66, 90 of FIGS. 9-19 and 20-23 is that they may be used with a family of medical devices 12 that have different lengths while minimizing the number of components that must be changed to accommodate different length medical devices 12. For example, it may be possible to use the same restraining sheath 22, wires 20 and covering sheath 26 to manufacture delivery systems 66, 90 that are suitable for different length stents 12. If a universal deployment handle 14 is used that can pull the wires 20 different lengths depending on the length of the stent 12 that is used, such as a handle that winds up the wire 20, a common deployment handle 14 may also be used. Thus, it may be possible to accommodate an entire family of different length stents 12 by merely trimming and end 68, 92 of the inner catheter 24 to accommodate longer length stents 12.

Figure 9:
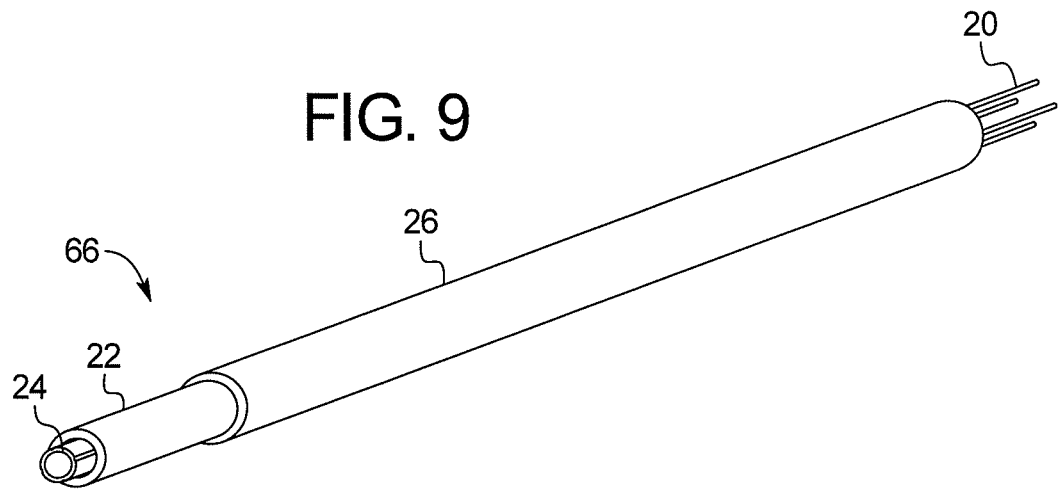
FIG. 9 is a perspective view of another delivery system, showing a covering sheath.

For example, FIG. 9 shows the delivery system 66 with a covering sheath 26 that extends over the proximal end of the restraining sheath 22 and extends proximally to the deployment handle 14 where it is fixed to the deployment handle like in FIG. 1. Thus, the covering sheath 26 does not move during deployment of the stent 12. The covering sheath 26 preferably does not extend over any part of the restraining sheath 22 that covers the stent 12. That is, since the covering sheath 26 preferably does not move during delivery, the covering sheath 26 in this case should only extend over the portion of the restraining sheath 22 located proximally from the stent 12 so that the covering sheath 26 does not interfere with expansion of the stent 12 when the restraining sheath 22 is withdrawn. It is also preferable for the covering sheath 26 and the restraining sheath 22 (illustrated in FIG. 10) to have inner and outer circumferences that are generally constant along the entire length of the covering sheath 26 and restraining sheath 22. This allows the length of the restraining sheath 22 to be shorter in length relative to a restraining sheath 22 like FIG. 1, since the proximal end of the restraining sheath 22 can be closer to the proximal end of the stent 12. For example, it may be preferable for the restraining sheath 22 to be about 1.5 times or less as long as the longest stent 12 in the family of stents 12. However, the restraining sheath 22 must be at least as long as the longest stent 12 in the family and longer than the shortest stent 12 in the family in order to use a common restraining sheath 22 in the delivery system 66, 90. Thus, like FIG. 1, the length of the restraining sheath 22 extends from the distal end of the stent 12 and terminates distally from the deployment handle 14 and prevents the stent 12 from self-expanding prior to deployment.

Figure 10:
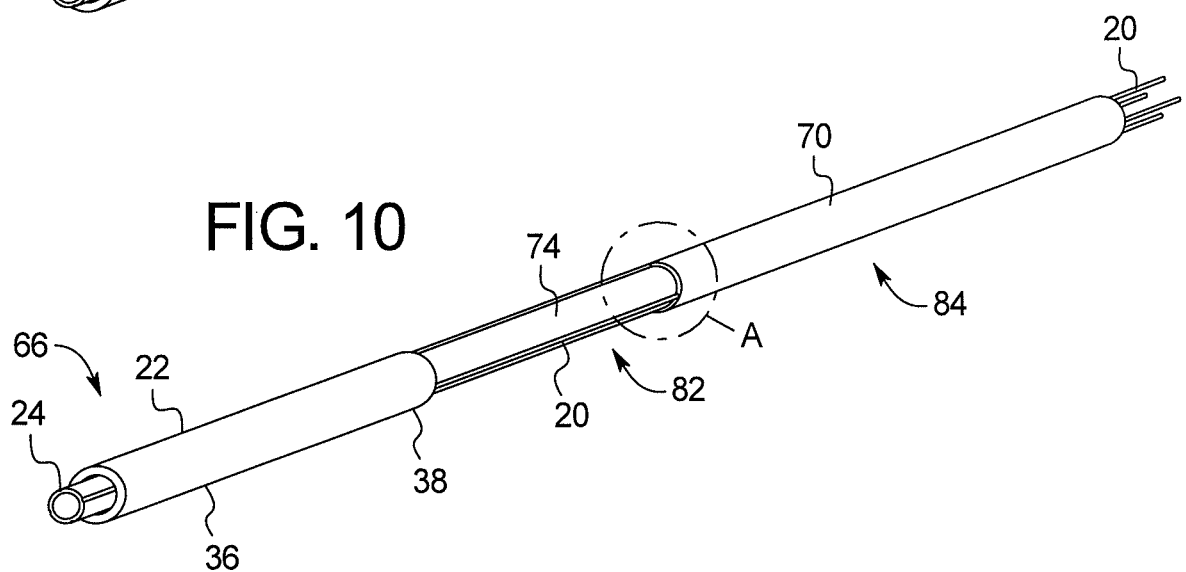
FIG. 10 is a perspective view of the delivery system, showing a restraining sheath, wires, a spacer tube and an inner catheter.
Figure 12:
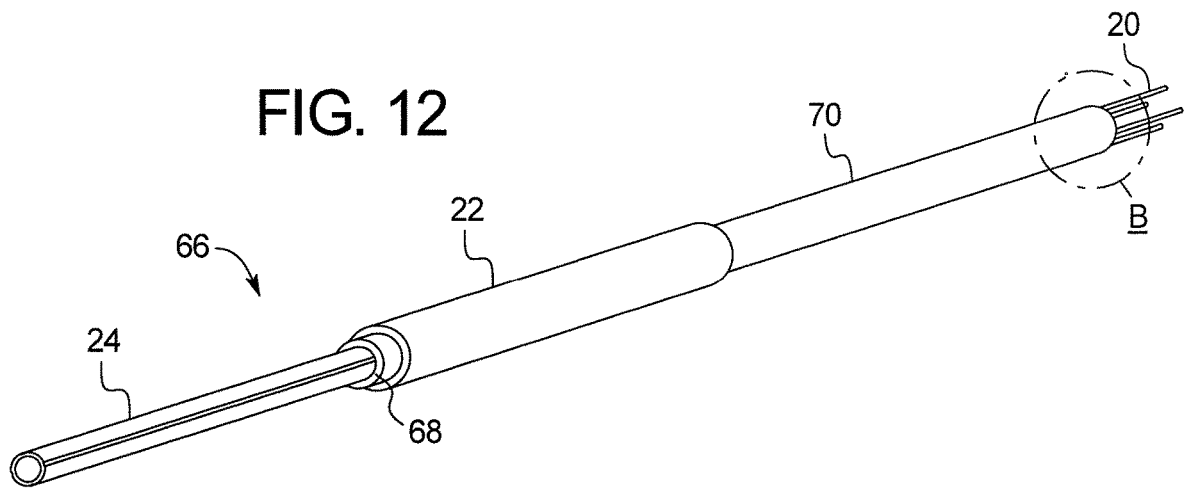
FIG. 12 is a perspective view of the delivery system, showing the restraining sheath withdrawn.

As shown in FIGS. 10 and 12, the wire 20 is adhered to the restraining sheath 22 and extends from the proximal end of the restraining sheath 22 to the deployment handle 14. In order to use a common restraining sheath 22, the longitudinal space between the restraining sheath 22 and the deployment handle 14 must be at least as long as the longest stent 12 in the family to allow enough space for the restraining sheath 22 to be withdrawn from the stent 12. Thus, as shown in FIG. 12, the stent 12 is deployed by pulling the wires 20 proximally to withdraw the restraining sheath 22.

Figure 14:
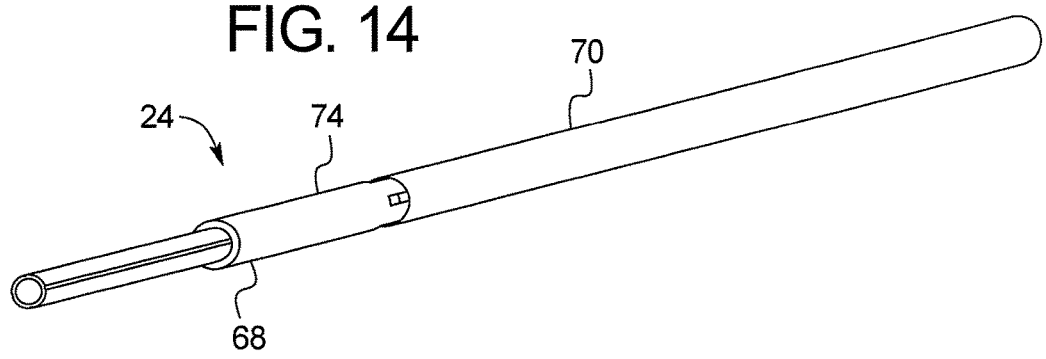
FIG. 14 is a perspective view of the spacer tube and the inner catheter.

As shown FIGS. 12 and 14, the inner catheter 24 has a distal-facing end 68 that either directly forms a stop surface 68 or supports a stop surface 68, such as a metal or polymer ring. The stop surface 68 abuts the proximal end of the stent 12 to prevent the stent 12 from moving proximally as the restraining sheath 22 is withdrawn. In order to accommodate stents 12 with different lengths while using a common restraining sheath 22 and common wires 20 (illustrated in FIG. 17), the distal-facing end 68 that forms or supports the stop surface 68 may be trimmed during manufacturing based on the length of each stent 12. Thus, the end 68 of the inner catheter 24 is trimmed so that when the proximal end of each stent 12 abuts the stop surface 68, the distal end of each stent 12 in the family is positioned at the same general position regardless of the length of each stent 12.

As shown in FIGS. 11, 14-16 and 18-19, this may be done by providing the inner catheter body 70 with a step 72 and providing a tube 74 that slides over the distal portion of the inner catheter body 70 until the proximal end 76 of the tube 74 abuts the step 72. In this embodiment, the step 72 may be located at a common position so that the same inner catheter body 70 can be used for all delivery systems 66 in the family. The inner catheter 24 is thus trimmed to length by trimming the distal end 78 of the tube 74 to the appropriate length. As a result, after the tube 74 is trimmed and slid onto the inner catheter body 70, the distal end 78 of the tube 74 forms or supports the stop surface 68 for the stent 12. Preferably, the tube 74 is made from plastic, such as polyether ether ketone (PEEK), and is preferably at least 5 mm long even when trimmed for the longest stent 12 in the family.

Figure 11:
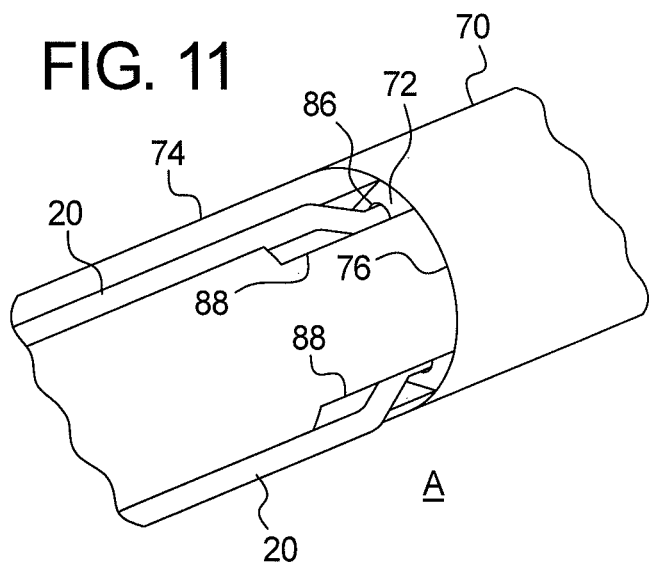
FIG. 11 is an enlarged perspective view of area A from FIG. 9, showing a joint between the spacer tube and the inner catheter.
Figure 13:
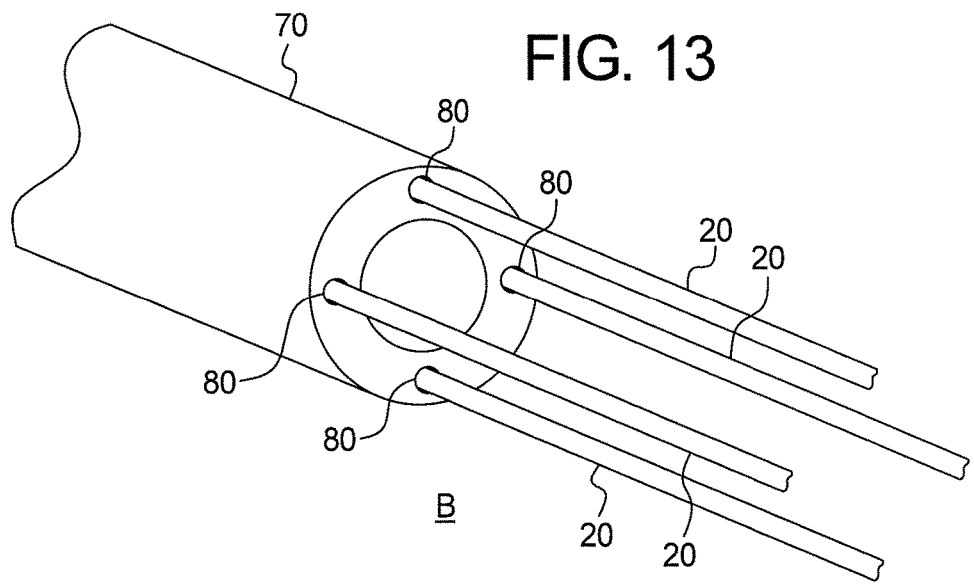
FIG. 13 is an enlarged perspective view of area B from FIG. 11, showing the wires extending from the proximal end of the inner catheter.
Figure 16:
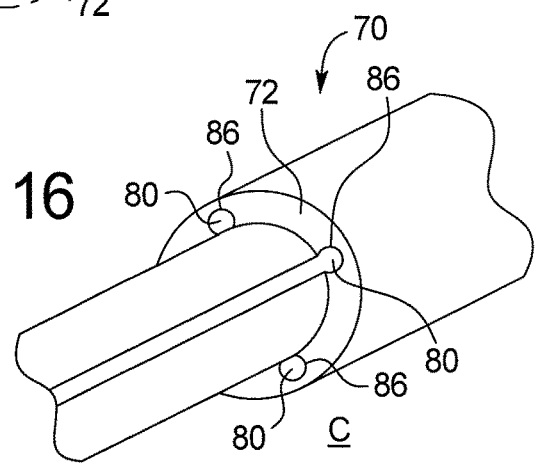
FIG. 16 is an enlarged perspective view of area C from FIG. 14.
Figure 17:
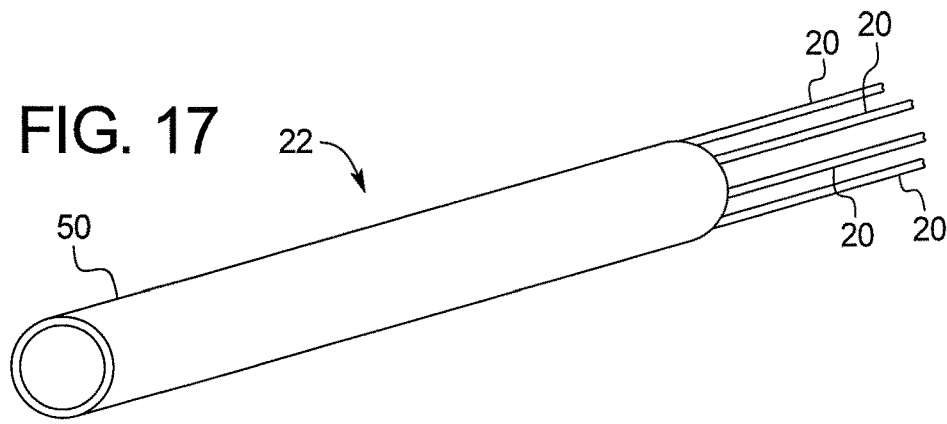
FIG. 17 is a perspective view of the restraining sheath and the wires.
Figure 18:
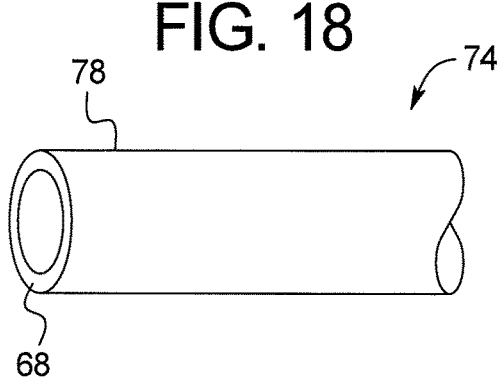
FIG. 18 is a perspective view of the distal end of the spacer tube.

As shown in FIGS. 11, 13 and 16, it may also be desirable for the wires 20 to extend through corresponding passageways 80 in the inner catheter 24 along a majority of the length between the deployment handle 14 and the restraining sheath 22. This may be desirable to ensure that the wires 20 stay separated from each other and do not get entangled with each other or interfere with each other when the restraining sheath 22 is withdrawn. For example, the delivery system 66, 90 may curve around various bends in the anatomy, and without the wires 20 being restrained and separated from each other, the wires 20 would tend to pull toward the inner side of the curve. Although a restraining sheath 22 with a single wire 20 may benefit from having the wire 20 extend through a passageway 80, 104 in the inner catheter 24, passageways 80, 104 for the wires 20 may be especially useful where two or more wires 20 are used to keep the wires 20 separated from each other as explained. While a single wire 20 may be used for the delivery system 10, 66, 90, in most cases two or more wires 20 will be used to balance the withdrawing force around the circumference of the restraining sheath 22.

As shown in FIGS. 13 and 16, the passageways 80 may be closed. That is, each passageway 80 fully encloses the circumference of each wire 20 along a portion of the length between the restraining sheath 22 and the deployment handle 14. In contrast, as described further below and shown FIGS. 22-23, the passageways 104 may also be open, such that at least part of the outer side of each wire 20 is uncovered by the passageway 104. As shown in FIG. 10, each of the wires 20 may be unenclosed along a first length 82 proximal from the restraining sheath 22. The first unenclosed length 82 will typically be at least as long as the stent 12 being delivered to allow the restraining sheath 22 to be fully withdrawn from the stent 12. Preferably, the first length 82 may be about 2 times the length of the stent 12 being delivered or less. The wires 20 are preferably enclosed within corresponding passageways 80 along a second length 84 proximal from the first length 82. The second length 84 may be a majority of the length between the deployment handle 14 and the restraining sheath 22, or may be the entire length between the deployment handle 14 and the first length 82.

Figure 15:
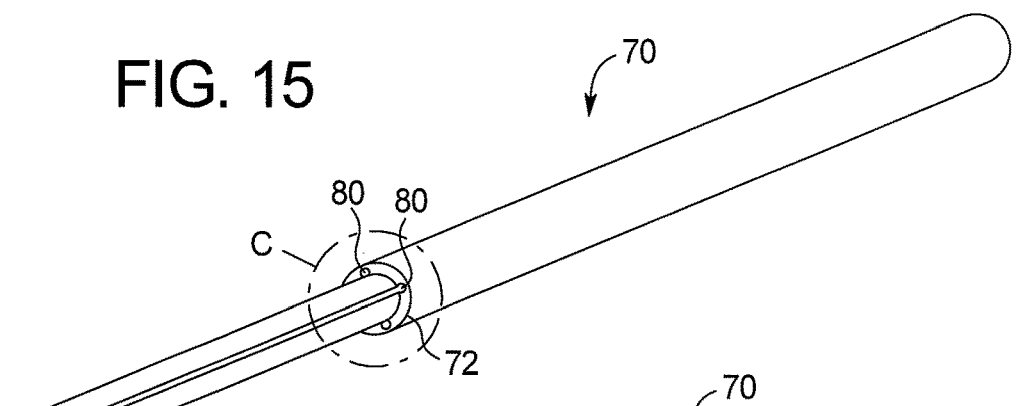
FIG. 15 is a perspective view of the inner catheter.
Figure 19:
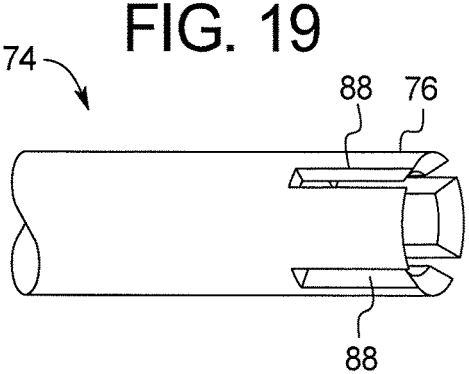
FIG. 19 is a perspective view of the proximal end of the spacer tube.

As shown in FIGS. 11 and 15-16, the wires 20 may enter the passageways 80 through distal openings 86 formed through the step 72 on the inner catheter 24. As shown in FIG. 11, the wires 20 may angle inward from the retention sheath 22 along the first length 82 to enter the passageways 80. As shown in FIGS. 11 and 19, the proximal end 76 of the tube 74 may be provided with recesses 88 to allow the wires 20 to extend through the recesses 88 to enter the passageways 80. The recesses 88 may be aligned with the distal openings 86 of the passageways 80 by inserting positioning mandrels through the distal openings 86 before the tube 74 is slid onto the inner catheter body 70. Thus, as the tube 74 is slid onto the inner catheter body 70, the outwardly extending, exposed portion of each positioning mandrel will guide the recesses 88 to line up the recesses 88 and the passageways 80. It may also be preferable to bond the tube 74 to the inner catheter body 70 at the proximal end 76 of the tube 74 and at the step 72 on the inner catheter body 70. This may be done by applying adhesive to the proximal end 76 of the tube 74 and the step 72 as the tube 74 is slid onto the inner catheter body 70. The positioning mandrels also may prevent the adhesive from entering the passageways 80 during bonding. The closed passageways 80 of FIGS. 13 and 16 may be formed in any suitable manner, but it may be preferred to make the inner catheter body 70 by extruding the inner catheter body 70 and forming the passageways 80 and the guide wire lumen 32 during the extrusion process. The step 72 on the inner catheter body 70 may also be formed by various methods, but centerless grinding may be a preferred method. Where the step 72 is formed by centerless grinding, the step 72 may have a slight taper as shown in FIG. 16, and the proximal end 76 of the tube 74 may be provided with a corresponding inward taper. Although various materials may be used for the inner catheter body 70, one possible material is polyether ether ketone (PEEK).

Another embodiment of the delivery system 90 is shown in FIGS. 20-23. For conciseness, features of the delivery systems 10, 66 that have been described above are not repeated below, since one of ordinary skill in the art will recognize that principles described above could be used with different delivery systems including the delivery system 90 of FIGS. 20-23. In this embodiment, the end 92 of the inner catheter 24 which is trimmed to accommodate stents 12 of different lengths may be integral with the length of the inner catheter 24 that forms the inner catheter body 94. For example, in FIG. 21, the very end 92 of the inner catheter body 94 could be the end 92 that supports or forms the stop surface 92. Thus, the inner catheter body 94 itself may be trimmed to length depending on the length of the stent 12 being loaded into the delivery system 90. Although various materials may be used for the inner catheter body 94, the inner catheter body 94 may be made from polyether ether ketone (PEEK), since the trimmed end 92 may be durable enough to form the stop surface 92 without requiring a separate metal or polymer ring for the stop surface 92. In this embodiment, the portion of the inner catheter 24 that extends through the stent 12 and is attached to the atraumatic tip 96 may be a separate liner 98 that extends through the lumen of the inner catheter body 94 and extends distally past the stop surface 92 to the atraumatic tip 96. Preferably, the liner 98 extends proximally to the deployment handle 14 and is fixed to the inner catheter body 94 at the deployment handle 14. Thus, in this arrangement, the liner 98 forms the guidewire lumen 32, and preferably a lubricious liner 98 may be used, such as polytetrafluoroethylene (PTFE). Although the liner 98 may be bonded along the length of the inner catheter body 94, the liner 98 may also float unattached within the lumen of the inner catheter body 94 and may be attached to the inner catheter body 94 at the deployment handle 14.

One advantage of using a separate liner 98 attached to the atraumatic tip 96 is that the tip 96 may be located closer to the proximal end of the stent 12 without needing to leave extra space at the distal end as is conventionally done during manufacturing when gluing the tip 96 onto the inner catheter 24. For example, in this arrangement, the tip 96 may be glued to the distal end of the liner 98 before the liner 98 is positioned within the lumen of the inner catheter body 94. The liner 98 may then be inserted into the central lumen of the inner catheter body 94 after the stent 12 is loaded into the restraining sheath 22, and the stent 12 and restraining sheath 22 are positioned on the inner catheter body 94. This allows the tip 96, which will form the leading end of the delivery system 90, to be positioned next to the distal end of the stent 12 after the tip 96 has been attached to the liner 98. As a result, the manufacturing assembler does not need to leave extra space to provide access for gluing and to prevent wet adhesive from contacting the stent 12.

Like the delivery system 66 of FIGS. 10 and 12, the delivery system 90 shown in FIGS. 20-21 may have a restraining sheath 22 with inner and outer circumferences that are generally constant along the entire length of the restraining sheath 22. As a result, the second portion of the restraining sheath 38 that extends proximally from the proximal end of the stent 12 may be shorter than the length of the stent 12 and may be shorter than the first portion 36 of the restraining sheath 22 which extends along the length of the stent 12. Like FIG. 9, this allows the covering sheath 26 shown in FIGS. 20-21 to also have inner and outer circumferences that are constant along the entire length of the covering sheath 26.

Figure 22:
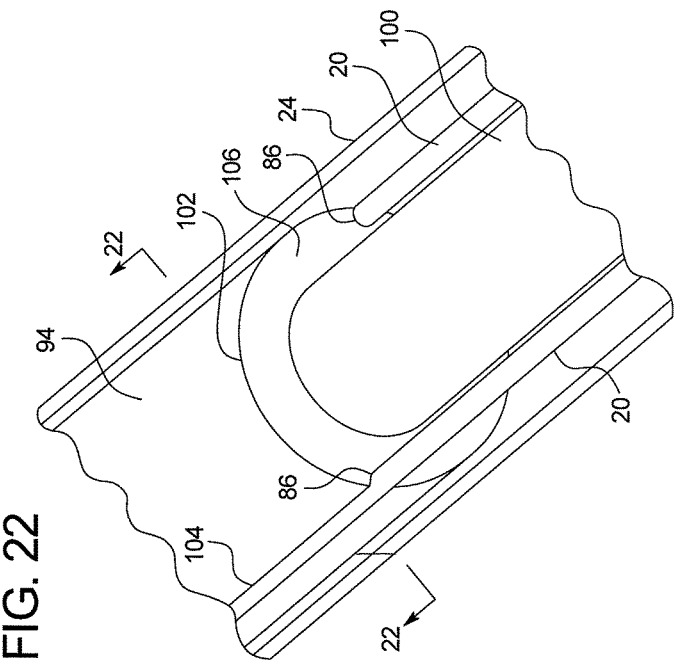
FIG. 22 is a perspective view of a portion of the delivery system, showing the inner catheter and the wires extending through open passageways.

As shown in FIGS. 21-22, the inner catheter 24 may be provided with a first outer circumference 100 that extends proximally from the stop surface 92 along a length at least as long as the length of the stent 12. The inner catheter 24 may also have a second outer circumference 102 extending proximally from the first outer circumference 100 along a length that is at least a majority of the length between the deployment handle 14 and the first outer circumference 100. Preferably, the second outer circumference 102 extends along the entire length from the deployment handle 14 to the first outer circumference 100. As shown, the second outer circumference 102 may be larger than the first outer circumference 100. The first outer circumference 100 is sized to be smaller than the inner circumference of the restraining sheath 22 so that the restraining sheath 22 can slide proximally over the first outer circumference 100 of the inner catheter 24. The second outer circumference 102 may be sized larger than the inner circumference of the restraining sheath 22 since the restraining sheath 22 only needs to be withdrawn a sufficient distance to release the stent 12 and is typically not withdrawn all the way proximally to the deployment handle 14.

An advantage of increasing the size of the second outer circumference 102 is that the clearance between the second outer circumference 102 and the covering sheath 26 can be reduced. For example, the clearance per side between the second outer circumference 102 and the inner circumference of the covering sheath 26 may be about 0.0005" or less. By increasing the size of the second outer circumference 102, the strength of the inner catheter 24 may be increased, both by the increased size of the second outer circumference 102 and by the covering sheath 26 reinforcing the inner catheter 24. Thus, the inner catheter 24 may be less likely to buckle and snake within the covering sheath 26 when compressive force is applied to the inner catheter 24 during deployment of the stent 12. In addition, because the covering sheath 26 does not move relative to the inner catheter 24 during deployment, the clearance between the second outer circumference 102 and the covering sheath 26 may be less than what would typically be needed to allow low friction sliding between components. For example, in a conventional delivery system, the restraining sheath extends proximally all the way to the deployment handle and slides along the entire length of the inner catheter during deployment. In that arrangement, sufficient clearance is required to allow low friction sliding between the restraining sheath and the inner catheter. Likewise, the clearance between the second outer circumference 102 and the inner circumference of the covering sheath 26 may be less than the clearance between the outer circumference of the restraining sheath 22 and the inner circumference of the covering sheath 24.

Figure 23:
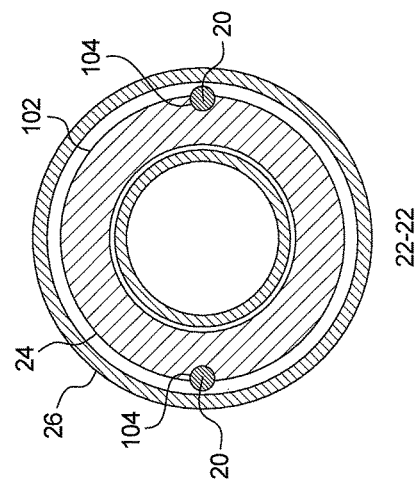
FIG. 23 is a cross-sectional view of the delivery system.

As shown in FIGS. 22-23, the passageways 104 extending through the inner catheter 24 for the wires 20 may be open as contrasted with the closed passageways 80 of FIGS. 11 and 13. In other words, the wires 20 may slide through passageways 104 that surround the inner circumference of each wire 20 while the outer circumference of each wire 20 is uncovered by the passageway 104. As shown in FIG. 22, the distal opening 86 of each passageway 104 may be formed through the step 106 where the second outer circumference 102 of the inner catheter 24 starts. As shown in FIGS. 20-21, the wires 20 may be unenclosed along the first outer circumference 100 of the inner catheter 24 from the proximal end of the restraining sheath 22. The unenclosed length is preferably at least as long as the length of the stent 12 to allow the restraining sheath 22 to fully withdraw from the stent 22 without interfering with the passageways 104. However, like FIG. 10, the unenclosed length is preferably no more than about 2 times as long as the stent 12. Preferably, the wires 20 extend substantially straight from the restraining sheath 22 to the distal openings 86 of the passageways 104. Each of the wires 20 extends through a corresponding open passageway 104 along a majority of the length from the deployment handle 14 to the restraining sheath 22. The wires 20 may also extend along the second outer circumference 102 through passageways 104 the entire length between the deployment handle 14 and the first outer circumference 100. The passageways 104 may be formed in the second outer circumference 102 in any suitable manner including extruding the passageways 104 during forming of the inner catheter 24 or grinding the passageways 104 into the second outer circumference 102. Although the passageways 104 in FIGS. 20-23 are open, the clearance between the inner catheter 24 and the covering sheath 26 may be sized to prevent the wires 20 from coming out of the passageways 104 as shown in FIG. 23. For example, if the delivery system 90 has at least two wires 20 equally spaced around the inner catheter 24, at least one third of the depth of each wire 20 may be disposed within each passageway 104 and the clearance per side between the second outer circumference 102 and the inner circumference of the covering sheath 26 may be about one third or less of the depth of each wire 20.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

What is claimed is:

1. A self-expanding medical device delivery system, comprising:
    a self-expanding medical device comprising a distal end, a proximal end and a length therebetween;
    an inner catheter extending proximally from said medical device to a deployment handle, said inner catheter comprising a stop surface adjacent said proximal end of said medical device and adapted to prevent said medical device from moving proximally during deployment of said medical device;
    a restraining sheath extending over said medical device and adapted to prevent said medical device from self-expanding prior to deployment of said medical device, said restraining sheath comprising an inner circumference and an outer circumference that are both generally constant along an entire length of said restraining sheath, and a proximal end of said restraining sheath terminating distally from said deployment handle; and
    a wire adhered to said restraining sheath and extending proximally from said restraining sheath to said deployment handle;
    wherein said medical device is deployed by pulling said wire proximally to withdraw said restraining sheath proximally away from said medical device;
    wherein said inner catheter comprises a first outer circumference extending proximally from said stop surface along a first length at least as long as said length of said medical device, and a second outer circumference extending proximally from said first length along a second length at least a majority of a length between said deployment handle and said first length, said first outer circumference being smaller than said inner circumference of said restraining sheath, and said second outer circumference being larger than said inner circumference of said restraining sheath.

2. The self-expanding medical device delivery system according to claim 1, further comprising a covering sheath extending from said restraining sheath to said deployment handle, said covering sheath extending over at least said proximal end of said restraining sheath, and wherein a clearance per side between said second outer circumference of said inner catheter and an inner circumference of said covering sheath is about 0.0005" or less.

3. The self-expanding medical device delivery system according to claim 1, wherein said wire extends through an open passageway formed along a length of said inner catheter, and said open passageway being formed along said second outer circumference.

4. The self-expanding medical device delivery system according to claim 3, further comprising a covering sheath extending from said restraining sheath to said deployment handle, said covering sheath extending over at least said proximal end of said restraining sheath, and at least two of said wires equally spaced around said inner catheter, wherein at least about a ⅓ of a depth of each wire is disposed within each open passageway and a clearance per side between said second outer circumference of said inner catheter and an inner circumference of said covering sheath is about ⅓ or less of said depth of each wire.

5. The self-expanding medical device delivery system according to claim 1,
    wherein said medical device is a stent, said restraining sheath comprises a first portion extending along said length of said medical device and a second portion extending proximally from said proximal end of said medical device to said proximal end of said restraining sheath, said second portion being at least as long as said length of said medical device, further comprising a covering sheath extending from said restraining sheath to said deployment handle, said covering sheath extending over at least said proximal end of said restraining sheath, and wherein said covering sheath comprises an inner circumference and an outer circumference that are both generally constant along an entire length of said covering sheath;
    wherein said covering sheath is fixed to said deployment handle and does not move during deployment of said medical device, said covering sheath extending over only a portion of said restraining sheath disposed proximally from said medical device.

6. The self-expanding medical device delivery system according to claim 5, wherein said wire extends through an open passageway formed along said second outer circumference of said inner catheter.

7. The self-expanding medical device delivery system according to claim 6, further comprising at least two of said wires equally spaced around said inner catheter, wherein a clearance per side between said second outer circumference of said inner catheter and an inner circumference of said covering sheath is about 0.0005" or less, at least about a ⅓ of a depth of each wire is disposed within each open passageway and said clearance per side between said second outer circumference of said inner catheter and said inner circumference of said covering sheath is about ⅓ or less of said depth of each wire, and a distal end of said covering sheath comprises an atraumatic taper and a close fitting inner diameter around said restraining sheath that presents a smooth transition between said restraining sheath and said covering sheath.

8. The self-expanding medical device delivery system according to claim 7, wherein said wire extends only along said second portion of said restraining sheath, and further comprising a low friction liner adhered to said restraining sheath and extending along said length of said medical device and contacting an outer surface of said medical device, wherein said restraining sheath comprises a thermoplastic polymer covering said wire and said liner, said inner catheter comprises a guidewire lumen extending from a distal end of said inner catheter to said deployment handle, and said wire comprises a coiled portion and a straight portion extending generally parallel to an axis of said coiled portion, said coiled portion being adhered to said restraining sheath and said straight portion extending proximally from said restraining sheath to said deployment handle.

9. A self-expanding medical device delivery system, comprising:
a self-expanding medical device comprising a distal end, a proximal end and a length therebetween;
an inner catheter extending proximally from said medical device to a deployment handle, said inner catheter comprising a stop surface adjacent said proximal end of said medical device and adapted to prevent said medical device from moving proximally during deployment of said medical device;
a restraining sheath extending over said medical device and adapted to prevent said medical device from self-expanding prior to deployment of said medical device, said restraining sheath comprising an inner circumference and an outer circumference that are both generally constant along an entire length of said restraining sheath, and a proximal end of said restraining sheath terminating distally from said deployment handle; and
a wire adhered to said restraining sheath and extending proximally from said restraining sheath to said deployment handle;
wherein said medical device is deployed by pulling said wire proximally to withdraw said restraining sheath proximally away from said medical device;
wherein said wire comprises a coiled portion and a straight portion extending generally parallel to an axis of said coiled portion, said coiled portion being adhered to said restraining sheath and said straight portion extending proximally from said restraining sheath to said deployment handle.

10. The self-expanding medical device delivery system according to claim 9, wherein said medical device is a stent, said restraining sheath comprises a first portion extending along said length of said medical device and a second portion extending proximally from said proximal end of said medical device to said proximal end of said restraining sheath, said second portion being at least as long as said length of said medical device, further comprising a covering sheath extending from said restraining sheath to said deployment handle, said covering sheath extending over at least said proximal end of said restraining sheath, and wherein said covering sheath comprises an inner circumference and an outer circumference that are both generally constant along an entire length of said covering sheath.

* * * * *